United States Patent [19]  [11] 4,342,773
Di Toro et al.  [45] Aug. 3, 1982

[54] N-ARYL-1,3-OXAZOLIDINE-2,4-DIONES EXERTING A FUNGICIDAL, SYSTEMIC ACTION IN THE FIELD

[75] Inventors: Vincenzo Di Toro, Como; Franco Gozzo, S. Donato Milanese; Mirella Cecere, Milan; Simone Lorusso, San Giuliano Milanese; Carlo Garavaglia, Cuggiono, all of Italy

[73] Assignee: Montedison S.p.A., Italy

[21] Appl. No.: 124,733

[22] Filed: Feb. 26, 1980

Related U.S. Application Data

[63] Continuation-in-part of Ser. No. 13,404, Feb. 21, 1979, abandoned.

[30] Foreign Application Priority Data

Feb. 24, 1978 [IT] Italy .............................. 20579 A/78

[51] Int. Cl.³ .................... A01N 43/76; C07D 263/04
[52] U.S. Cl. ...................................... 424/272; 548/226
[58] Field of Search ......................... 548/226; 424/272

[56] References Cited
U.S. PATENT DOCUMENTS

T903,025 10/1972 Machiele .............................. 96/100
3,280,136 10/1966 Finkbeiner ........................ 548/226
3,966,750 6/1976 Mangold et al. .................... 548/226

FOREIGN PATENT DOCUMENTS 2207576 8/1973 Fed. Rep. of Germany .
1247527 9/1971 United Kingdom .

Primary Examiner—Anton H. Sutto

Attorney, Agent, or Firm—Stevens, Davis, Miller & Mosher

[57] ABSTRACT

There are disclosed N-aryl-1,3-oxazolidine-2,4-diones of the formula:

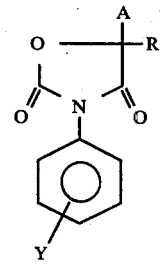

wherein:
R = $C_1$–$C_5$ alkyl; $C_1$–$C_5$ haloalkyl
Y = H; hydrogen, 3,4-dichloro; 3,5-dichloro; 3,5-difluoro; 3,5-dimethyl; 3,5-dimethoxy; 3,5-bis-trifluoromethyl; and
A =

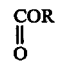

wherein R is as previously defined.

The N-aryl-1,3-oxazolidine-2,4-diones are useful fungicides, possess systemic action, and are particularly active in the field.

14 Claims, No Drawings

N-ARYL-1,3-OXAZOLIDINE-2,4-DIONES EXERTING A FUNGICIDAL, SYSTEMIC ACTION IN THE FIELD

CROSS-REFERENCE TO RELATED APPLICATIONS

This application is a continuation-in-part of copending application Ser. No. 13,404 filed Feb. 21, 1979, now abandoned.

BACKGROUND OF THE INVENTION

This invention relates to a new class of derivatives of N-aryl-1,3-oxazolidine-2,4-diones exerting a fungicidal action. More particularly, it relates to novel N-aryl-1,3-oxazolidine-2,4-diones substituted in the 5-position and to the utilization thereof for fighting infections in useful plants due to fungi.

DESCRIPTION OF THE PRIOR ART

Derivatives of N-(3,5-dichlorophenyl)-1,3-oxazolidine-2,4-dione substituted in the 5-position by two alkyl groups or by a hydrogen atom and an alkyl group, and exerting a fungicidal activity, are described in Dutch patent application No. 68/17249 of Sumitomo Company. According to BASF's French patent application No. 2,172,295, such compounds seem to have only a weak fungicidal activity, wherefore BASF describes derivatives of N-(3,5-dichlorophenyl)-1,3-oxazolidine-2,4-dione having in the 5-position two substituents, one of which is either H or alkyl, and the other of which is alkenyl, or both together represent a methylene group. It is known furthermore that the most representative compound among those described in the aforesaid Dutch patent application No. 68/17249, i.e. N-(3,5-dichlorophenyl)-5,5-dimethyl-1,3-oxazolidine-2,4-dione, available on the market under the trademark Sclex, has prejudicial secondary effects on humans.

On the other hand, a compound made in accordance with French patent application No. 2,172,295, i.e. N-(3,5-dichlorophenyl)-5-methyl-5-vinyl-1,3-oxazolidine-2,4-dione (trademark: Vinchlozoline), exhibits some difficulties in its synthesis which are connected with the necessity of prepared a β-γ unsaturated lactate.

The necessity of finding new compounds that are economically advantageous and efficient in defending important agrarian cultures from the attack of pathogenous fungi is the main reason for continuous and intensive research work in the field of the N-aryloxazolindiones.

GENERAL DESCRIPTION OF THE INVENTION

A new class of oxazolidine derivatives that are endowed with excellent fungicidal properties has been found.

Accordingly, it is a principal object of the present invention to provide new N-aryl-1,3-oxazolidine-2,4-diones differently substituted in the 5-position and particularly such N-phenyl derivatives.

A further object of the present invention is to establish the fungicidal activity and the systemic activity of the new N-aryl-1,3-oxazolidine-2,4-diones.

Another object of the present invention is to prove the particular usefulness of the new N-aryl-1,3-oxazolidine-2,4-diones in the field.

The compounds of the present invention have the general formula:

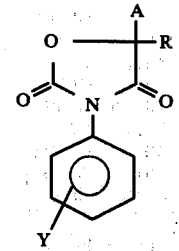

wherein:
R = $C_1$-$C_5$ alkyl; $C_1$-$C_5$ haloalkyl;
Y = H; halogen; 3,4-dichloro; 3,5-dichloro; 3,5-difluoro; 3,5-dimethyl; 3,5-dimethoxy; 3,5-bis-trifluoromethyl; and
A =

wherein R is as previously defined, i.e. $C_1$-$C_5$ alkyl or $C_1$-$C_5$ haloalkyl.

SPECIFIC DESCRIPTION OF THE INVENTION

Among the compounds which have proved so far to be the most interesting are those recorded in the following Table I:

TABLE I

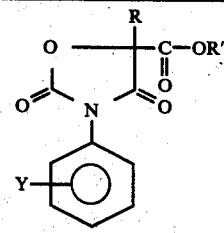

| Compound N° | SUBSTITUENTS | | | Melting Point °C. | Crystallization Solvent | ELEMENTAL ANALYSIS | | | | | |
|---|---|---|---|---|---|---|---|---|---|---|---|
| | | | | | | C % | | H % | | N % | |
| | Y | R | R¹ | | | calc. | found | calc. | found | calc. | found |
| 1 | H | CH₃ | OC₂H₅ | 103–6 | ethanol | 59.31 | 58.63 | 4.98 | 4.90 | 5.32 | 5.24 |
| 2 | 3-Cl | CH₃ | OC₂H₅ | 88–90 | " | 52.45 | 53.62 | 4.06 | 4.13 | 4.70 | 5.00 |
| 3 | 4-Cl | CH₃ | OC₂H₅ | 94–97 | " | 52.45 | 52.65 | 4.06 | 4.14 | 4.70 | 4.63 |
| 4 | 3,5-Cl₂ | CH₃ | OC₂H₅ | 109–10 | " | 47.01 | 47.22 | 3.34 | 3.32 | 4.22 | 4.40 |
| 5 | 3,4-Cl₂ | CH₃ | OC₂H₅ | 78–80 | " | 47.01 | 47.90 | 3.34 | 3.40 | 4.22 | 4.20 |
| 6 | 3,5-(CH₃)₂ | CH₃ | OC₂H₅ | 112–4 | " | 61.80 | 62.40 | 5.90 | 5.80 | 4.80 | 4.80 |

TABLE I-continued

| Compound N° | SUBSTITUENTS Y | R | R¹ | Melting Point °C. | Crystal- lization Solvent | C % calc. | C % found | H % calc. | H % found | N % calc. | N % found |
|---|---|---|---|---|---|---|---|---|---|---|---|
| 7  | 3,5-(OCH$_3$)$_2$ | CH$_3$   | OC$_2$H$_5$   | 110-1   | "        | 55.73 | 55.64 | 5.30 | 5.30 | 4.33 | 4.76 |
| 8  | 3,5-(CF$_3$)$_2$  | CH$_3$   | OC$_2$H$_5$   | 115-7   |          |       |       |      |      | 3.51 | 3.45 |
| 9  | 3,5-Cl$_2$        | C$_2$H$_5$ | OC$_2$H$_5$ | 90-4    | "        | 48.58 | 48.88 | 3.78 | 3.69 | 4.05 | 4.11 |
| 10 | 3,5-Cl$_2$        | CH$_3$   | OC$_3$H$_7$n  | 75-9    | "        | 48.58 | 49.39 | 3.78 | 4.14 | 4.05 | 3.88 |
| 11 | 3,5-Cl$_2$        | CH$_3$   | OC$_3$H$_7$iso| 95-8    | "        | 48.58 | 48.44 | 3.78 | 3.89 | 4.05 | 4.10 |
| 12 | 3,5-(CH$_3$)$_2$  | H        | OC$_2$H$_5$   | 62-4    | methanol | 60.64 | 60.64 | 5.45 | 5.57 | 5.05 | 4.93 |
| 13 | 3,5-(OCH$_3$)$_2$ | H        | OC$_2$H$_5$   | —       |          | 54.37 | 54.41 | 4.89 | 5.34 | 4.53 | 4.40 |
| 14 | 3,5-(CF$_3$)$_2$  | H        | OC$_2$H$_5$   | 118-20  | ethanol  |       |       |      |      | 3.64 | 3.56 |
| 15 | 3,5-Cl$_2$        | H        | OC$_2$H$_5$   | 90-92   | "        | 45.31 | 45.70 | 2.85 | 2.88 | 4.40 | 4.34 |
| 16 | 3,5-Cl$_2$        | CH$_3$   | OCH$_3$       | 127-9   | "        | 45.31 | 45.86 | 2.85 | 2.94 | 4.40 | 4.45 |
| 17 | 3,5-(CH$_3$)$_2$  | CH$_3$   | OCH$_3$       | 117-118 | EtOH     | 54.37 | 54.97 | 4.89 | 5.01 | 4.53 | 4.59 |
| 18 | 3,5-(Cl)$_2$      | CH$_2$Br | OC$_2$H$_5$   | 146     | EtOH     | 37.99 | 38.31 | 2.45 | 2.33 | 3.41 | 3.14 |
| 19 | 2-F               | CH$_3$   | OC$_2$H$_5$   | oil     | —        | —     | —     | —    | —    | 4.98 | 5.02 |
| 20 | 3-F               | CH$_3$   | OC$_2$H$_5$   | 79      | EtOH     | —     | —     | —    | —    | 4.98 | 4.90 |
| 21 | 3,5-(F)$_2$       | CH$_3$   | OC$_2$H$_5$   | 97-98   | EtOH     | —     | —     | —    | —    | 4.68 | 4.24 |
| 22 | 3,5-(Cl)$_2$      | C$_2$H$_5$ | OCH$_3$     | 120-121 | MeOH     | 47.01 | 47.00 | 3.34 | 3.28 | 4.22 | 4.22 |

The method of preparing the compounds of the present invention consists essentially of reacting α-hydroxy-esters or analogs thereof having the general formula:

$$R^2-\overset{O}{\overset{\|}{C}}-\overset{OH}{\underset{R}{\overset{|}{C}}}-A \quad (II)$$

(wherein A and R have the same meanings as given above in general formula I and $R^2$=OH, OR, or NH$_2$), with an aryl-isocyanate in the presence of a tertiary base, which favors the ring-closing of the carbamate intermediate.

The reaction is depicted schematically as follows:

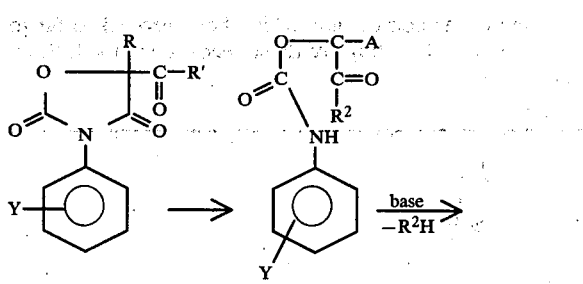

The α-hydroxy-esters of general formula II are derivatives easily obtainable from inexpensive raw materials.

The compounds of general formula I are endowed with a high fungicidal action, which is superior to that of the N-(3,5-dichlorophenyl)-1,3-oxazolidine-2,4-diones already known (see Tables II, III, IV). Moreover, the compounds of general formula I are endowed with systemic activity (see Example 3 infra) and therefore are able to migrate into the plant to combat plant infections due to fungi; and the compounds of general formula I show an improved activity in the field (see Example 4 infra).

The following examples are given to still better illustrate the present invention.

EXAMPLE 1

N-(3,5-dichlorophenyl)-5-methyl-5-carboethoxy-1,3-oxazolidine-2,4-dione. (Compound No. 4—Table I)

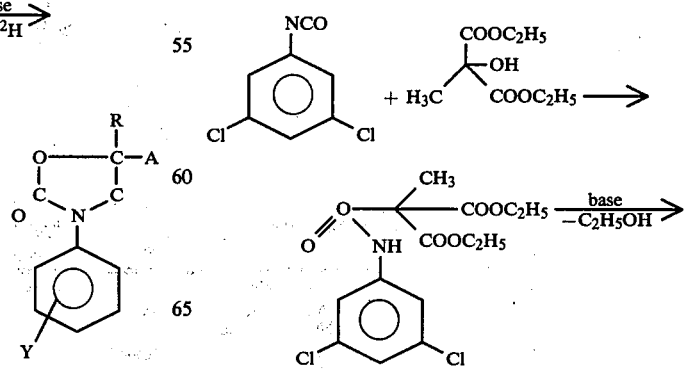

-continued

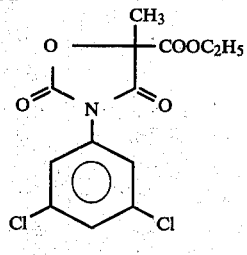

For the species Helminthosporium maydis, Helminthosporium oryzae, and Alternaria tenuis, 100 μl of a suspension of spores and mycelium were introduced into tubes containing 10 cc of potato broth (Difco), which were kept horizontally and in incubation for 7 days at 25° C. After the incubation period and after intense agitation, the percentage of growth inhibition of the fungi was calculated by placing the tubes vertically and close to one another.

The results obtained are recorded below in Table II.

TABLE II

| | Fungicidal activity in vitro | | | | | | |
|---|---|---|---|---|---|---|---|
| Compound No. | Fungus dose: Botrytis c. 5 ppm | Monilia fric. 5 ppm | Penicillium It. 25 ppm | Aspargillus par. 25 ppm | Helminthosporium Maydis 25 ppm | Helminthsporium oryzoe 25 ppm | Alternaria tenius 50 ppm |
| 16 | 100 | 100 | 100 | 100 | 100 | 100 | 100 |
| 4 | 100 | 100 | 100 | 100 | 100 | 100 | 100 |
| 9 | 100 | 100 | 100 | 100 | 100 | 100 | 100 |
| 10 | 100 | 100 | 100 | 100 | 100 | 100 | 100 |
| Sclex* | 100 | 100 | 80 | 70 | 60 | 70 | 30 |
| Vinchlozoline** | 100 | 100 | 100 | 100 | 100 | 100 | 80 |

| | Fungicidal activity in vitro on Botrytis c. | | |
|---|---|---|---|
| Compound No. Dose, ppm | 100 | 50 | 5 |
| 2 | 100 | 100 | 100 |
| 15 | 100 | 100 | 100 |
| 18 | 100 | 100 | 100 |
| 20 | 100 | 100 | 100 |
| 21 | 100 | 100 | 100 |
| 22 | 100 | 100 | 100 |

*N-(3,5-dichlorophenyl)-5,5-dimethyl-oxazolidine-2,4-dione (active principle of commercial product ¢Sclex")
**N-(3,5-dichlorophenyl)-5-methyl-5-vinyl-oxazolidine-2,4-dione (active principle of commercial product "Vinchlozoline")

37.6 g of 3,5-dichlorophenyl isocyanate and 38 g of diethylic methyl-tartronate (diethyl ester of 2-methyl-2-hydroxymalonic acid) were dissolved in 1 liter of benzene.

The resulting solution was stirred at room temperature for 3 hours whereupon, after addition of 1 ml of triethylamine, it was heated at reflux for 12 hours. The heated solution was then filtered and the solvent was evaporated under reduced pressure.

The solid residue was re-crystallized from ethyl alcohol. 45 g of product was thus obtained (white needles, m.p.=109°-110° C.).

(By an analogous procedure, the remaining compounds listed in Table I were synthetized).

EXAMPLE 2

Biological activity of the compounds of this invention.

(a) Activity in vitro.

The activity was determined by evaluating the percentage of growth of the fungi cultivated in soil containing increasing amounts of the compounds being tested. Such compounds were introduced into the culture medium in the form of dispersions with dimethyl sulphoxide+Tween 20, so as to give a final concentration of 0.5% in dimethyl sulphoxide and 0.01% in Tween 20.

For the species of fungi such as Botrytis cinerea, Monilia fructigena, Penicillium italicum, and Aspergillus parassiticum, 1 drop of a suspension of spores and mycelium was put in the center of Petri capsules containing agar-treated soil (PD Agar Difco) to yield a circular inoculum. After a 4-day growth at 25° C. the diameters of the colonies that had developed were measured, and the percentage of growth inhibition in respect to the untreated checks were calculated.

(b) Preventive activity against Botrytis cinerea on tomato plants

Both leaf faces of tomato plants cv. Marmande, cultivated in pot in a conditioned environment at 25° C. and 60% relative humidity, were sprinkled with an aqueous suspension of a formulation in the form of wetting powder of the products being tested at 20% by weight concentration until the leaves are uniformly wet.

After one day artificial infection was effected by inoculating a suspension of Botrytis cinerea in carrot broth (1,000,000 spores/cc) into both leaf faces. After a 24-hour residence period in a humidity-saturated environment at 26° C., the plants were transferred into an environment at 26° C. and 70% relative humidity for the duration of the incubation period (6 days).

Finally, the seriousness of the infection was visually evaluated according to indices on a measuring scale ranging from 100 (sound plant) to 0 (thoroughly-infected plant).

The results obtained are recorded in Table III.

TABLE III

| Preventive fungicidal activity against Botrytis c. on tomato plants | | | |
|---|---|---|---|
| Compound No. Dose, % o | 3 | 1.5 | 0.75 |
| 1 | 100 | 100 | 100 |
| 4 | 100 | 100 | 100 |
| 5 | 100 | 100 | 100 |
| 16 | 100 | 100 | 100 |
| 21 | 100 | 100 | 100 |
| Sclex (PB 50) (reference commercial product) | 100 | 97 | 96 |
| Vinchlozoline (PB 50) (reference commercial product) | 100 | 100 | 95 |

(c) Preventive activity against Plasmopara viticola on vine plants

The leaves of vine plants cv. Dolcetto, cultivated in pot in a conditioned environment at 25° C. and 60% relative humidity, were treated by spraying both faces of same with the products being tested in a hydroacetonic solution (20% of acetone vol./vol.), until the leaves are uniformly wet.

24 hours after the treatment, the lower faces of the leaves were spraying with an aqueous suspension of conidia of *Plasmopara viticola* (200,000 conidia/cc).

After a 24-hour period of residence in a humidity-saturated environment at 21° C., the plants were transferred to a 70% relative humidity at 21° C. for the incubation period (7days).

Finally, the intensity of the infection was evaluated according to indices of an evaluation scale ranging from 100 (sound plant) to 0 (fully infected plant).

The results obtained are recorded below in Table IV.

TABLE IV

Preventive fungicidal activity against *Plasmopara viticola* on vine plants

| Compound No. | Concentration, % o | 1 | 0.5 | 0.1 |
|---|---|---|---|---|
| 2 | | 100 | 100 | 100 |
| 7 | | 100 | 100 | 100 |
| 9 | | 100 | 100 | 100 |
| 10 | | 100 | 100 | 100 |
| 11 | | 100 | 100 | 100 |
| 13 | | 100 | 100 | 85 |
| Vinichlozoline (PB 50) (commercial product of reference) | | 100 | 95 | 80 |

EXAMPLE 3

Systemic, preventive fungicidal action in strawberry and tomato plants

Strawberry (cv. Souncrest) and tomato (cv. Marmande) plants grown in pots in a conditioned environment at 26° C. and 60% relative humidity were treated by adding to the soil an aqueous dispersion of the products under examination, each of which was formulated as a wetting powder with a 20% concentration of the active principle. The plants were kept in a conditioned environment and seven days after the treatment, both faces of the leaves were infected by sprinkling on them a suspension of *Botrytis cinerea conidia* in carrot broth (1,000,000 of conidia per ml.).

After an incubation period of 14 days for strawberry plants and 8 days for tomato plants, the infection was evaluated on a scale ranging from 0 (completely infected plant) to 100 (no infection).

The results are summarized in the following Table V.

TABLE V

Tests of systemic activity through roots adsorbance in tomato plants infected with *Botrytis cinerea* 7 days after soil treatment

| Compound No. | Dose % o | % activity |
|---|---|---|
| 4 | 3 | 100 |
| 10 | 3 | 100 |
| 21 | 3 | 80 |
| 22 | 3 | 100 |
| Sclex (PB 50) | 3 | 0 |
| Ronilan (PB 50) (Vinchlozoline) | 3 | 0 |
| Sumilex (PB 50) | 3 | 0 |

EXAMPLE 4

Field Test for the Protection of Vine Plants From *Botrytis cinerea*

In a field containing vine plants (cv. Moscato, 4 years old) divided into 3 groups of 5 plants each, 2 groups were treated 4 times with the fungicide compounds listed in Table VI infra in form of wetting powder containing 20% by weight of the active principle.

The treatment was carried out at the following times:

| A | End of blossoming |
| B | When the grapes come into contact with each other |
| C | When grape pigmentation appears |
| D | 20 days before the harvest |
| | The third group of 5 plants represented the control. |

The day after each treatment all plants (the treated ones and the control ones) were infected with a suspension of conidia of *Botrytis cinerea*, taking care to infect all the grapes.

Favorable conditions for the development of the infection were caused by a nebulization of water on all the vineyard during the entire testing period. At the harvest, the results were evaluated by counting the percent of grapes affected by the infection and expressing such percent as medium index of the infection.

The results are summarized in the following Table VI.

TABLE VI

Field test on vine plants (cv. Moscato) infected by *Botrytis cinerea*

| Compound No. | Dose g/hectare | Index of infection |
|---|---|---|
| 4 (PB 50) | 150 | 0.85 |
| Ronilan (PB 50) | 150 | 9.00 |
| Control | — | 45.20 |

What is claimed is:

1. An antifungal N-aryl-1,3-oxazolidine-2,4-dione, having systemic activity and improved usefulness in the field, of the formula:

$$\begin{array}{c}\text{structure with oxazolidine ring bearing substituents A and R at C-5, and N-aryl group with Y substituent}\end{array}$$

wherein:
R=$C_1$–$C_5$ alkyl; $C_1$–$C_5$-haloalkyl;
Y=H; halogen; 3,4-dichloro; 3,5-dichloro; 3,5-difluoro; 3,5-dimethyl; 3,5-dimethoxy; 3,5-bis-trifluoromethyl; and
A=

$$\begin{array}{c}\text{COR}\\ \parallel\\ \text{O}\end{array}$$

wherein R is as defined previously.

2. A method of fighting infestations due to fungi in useful plants, consisting essentially of treating said useful plants with a compound of claim 1, present in a solution containing said compound functioning as the active ingredient and present in an amount of at least 0.1% o.

3. The compound of claim 1 which is N-(3,5-dichlorophenyl)-5-methyl-5-carbomethoxy-1,3-oxazolidine-2,4-dione.

4. The compound of claim 1 which is N-(3,5-dichlorophenyl)-5-methyl-5-carboethoxy-1,3-oxazolidine-2,4-dione.

5. The compound of claim 1 which is N-(3,4-dichlorophenyl)-5-methyl-5-carboethoxy-1,3-oxazolidine-2,4-dione.

6. The compound of claim 1 which is N-(3,5-dichlorophenyl)-5-ethyl-5-carboethoxy-1,3-oxazolidine-2,4-dione.

7. The compound of claim 1 which is N-(3,5-difluorophenyl)-5-methyl-5-carboethoxy-1,3-oxazolidine-2,4-dione.

8. The compound of claim 1 which is N-(3,5-dimethoxyphenyl)-5-methyl-5-carboethoxy-1,3-oxazolidine-2,4-dione.

9. The compound of claim 1 which is N-(3,5-dimethylphenyl)-5-methyl-5-carboethoxy-1,3-oxazolidine-2,4-dione.

10. The compound of claim 1 which is N-(3,5-dichlorophenyl)-5-(1-bromomethyl)-5-carboethoxy-1,3-oxazolidine-2,4-dione.

11. The compound of claim 1 which is N-(3,5-dichlorophenyl)-5-ethyl-5-carbomethoxy-1,3-oxazolidine-2,4-dione.

12. The compound of claim 1 which is N-(phenyl)-5-methyl-5-carboethoxy-1,3-oxazolidine-2,4-dione.

13. The compound of claim 1 which is N-(3-chlorophenyl)-5-methyl-5-carboethoxy-1,3-oxazolidine-2,4-dione.

14. The compound of claim 1 which is N-(3,5-dichlorophenyl)-5-methyl-5-carbo-n-propoxy-1,3-oxazolidine-2,4-dione.

* * * * *